US010888529B2

(12) United States Patent
Sánchez Barreiro et al.

(10) Patent No.: US 10,888,529 B2
(45) Date of Patent: Jan. 12, 2021

(54) VEHICLES FOR THE TRANSFECTION OF MIRNAS

(71) Applicant: UNIVERSIDAD DEL PAIS VASCO-EUSKAL HERRIKO UNIBERTSITATEA (UPV/EHU), Leioa (ES)

(72) Inventors: Alejandro Sänchez Barreiro, Santiago de Compostela—la Coruña (ES); Inés Fernández Piñeiro, Santiago de Compostela—la Coruña (ES); Iker Badiola, Leioa (ES); Joana Märquez, Leioa (ES)

(73) Assignee: UNIVERSIDAD DEL PAIS VASCO-EUSKAL HERRIKO UNIBERTSITATEA, Leioa (ES)

( * ) Notice: Subject to any disclaimer, the term of this patent is extended or adjusted under 35 U.S.C. 154(b) by 0 days.

(21) Appl. No.: 16/091,071

(22) PCT Filed: Apr. 4, 2017

(86) PCT No.: PCT/ES2017/070205
§ 371 (c)(1),
(2) Date: Oct. 3, 2018

(87) PCT Pub. No.: WO2017/174847
PCT Pub. Date: Oct. 12, 2017

(65) Prior Publication Data
US 2019/0111002 A1    Apr. 18, 2019

(30) Foreign Application Priority Data

Apr. 5, 2016  (ES) .................................. 201630417

(51) Int. Cl.
| A61K 9/51 | (2006.01) |
| A61K 31/7105 | (2006.01) |
| B82B 3/00 | (2006.01) |
| A61K 47/18 | (2017.01) |
| B82Y 5/00 | (2011.01) |
| B82B 1/00 | (2006.01) |

(52) U.S. Cl.
CPC ........ *A61K 9/5123* (2013.01); *A61K 31/7105* (2013.01); *A61K 47/186* (2013.01); *B82B 1/00* (2013.01); *B82B 3/00* (2013.01); *B82Y 5/00* (2013.01)

(58) Field of Classification Search
None
See application file for complete search history.

(56) References Cited

U.S. PATENT DOCUMENTS

| 2011/0190383 A1* | 8/2011 | Marsh ................. C12Q 1/6883 514/44 A |
| 2014/0314852 A1* | 10/2014 | Sanchez Barreiro .... A61K 9/51 424/489 |
| 2014/0314857 A1* | 10/2014 | Holmes ................ A61K 31/351 424/490 |
| 2015/0065524 A1* | 3/2015 | Ren ...................... C07D 471/04 514/262.1 |

FOREIGN PATENT DOCUMENTS

| EP | 2386640 A2 | 11/2011 |
| EP | 2792350 A1 | 10/2014 |
| WO | 2008147974 A1 | 12/2008 |
| WO | 2013068625 A1 | 5/2013 |
| WO | 2015189429 A1 | 12/2015 |
| WO | 2016042187 A1 | 3/2016 |

OTHER PUBLICATIONS

André, E.M. et al., "Nano and microcarriers to improve stem cell behaviour for neuroregenrative medicine strategies: Application to Huntington's disease" Biomaterials, 2016, vol. 83, pp. 347-362.
Brandt, Marius R.G., et al. "Adenovirus vector-mediated RNA interference for the inhibition of human Parvovirus B19 replication" Virus Res, 2013, 176: 155-160.
Garzon, R., et al., "Targeting MicroRNAs in Cancer: Rationale, Strategies and Challenges" Nature Reviews, Drug Discovery, 2010, vol. 9 No. 10, pp. 775-789.
Gregoriadis, G. et al., "Polysialic acids: potential in improving the stability and pharmacokinetics of proteins and other therapeutics", Cell. Mol. Life Sci. 2000, vol. 57, pp. 1964-1969.
International Search Report for International Application No. PCT/ES2017/070205 filed on Apr. 4, 2017; dated Jun. 29, 2017; 4 pages.
Kasar, S., et al. "Systemic in vivo lentiviral delivery of rniR-15a/16 reduces malignancy in the NZB de novo mouse model of Chronic Lymphocytic Leukemia" Genes Immun, 2012, 13: 109-119.
Lam, J. KW., et al., "siRNA Versus miRNA as Therapeutics for Gene Silencing", Molecular Therapy—Nucleic Acids, 2015, vol. 4, pp. e252.
Rinkenauer, et al. "Comparison of the uptake of methacrylate-based nanoparticles in static and dynamic in vitro systems as well as in vivo", Journal of Controlled Release: Official Journal of the Controlled Release Society, 2015, vol. 216, pp. 158-168.
Sadauskas, E., et al. "Kupffer cells are central in the removal of nanoparticles from the organism" Particle and Fibre Toxicology, 2007, vol. 4, pp. 10.

(Continued)

*Primary Examiner* — Tracy Vivlemore
(74) *Attorney, Agent, or Firm* — Cantor Colburn LLP

(57) ABSTRACT

The invention relates to a nanoparticle comprising: (i) between 60 wt.-% and 99 wt.-% sorbitan ester, relative to the total weight of the nanoparticle; (ii) a positively charged substance; and (iii) a miRNA. The invention also relates to the methods for producing same and to the uses thereof, particularly for therapeutic uses, such as cancer treatment.

17 Claims, 6 Drawing Sheets

(56) References Cited

OTHER PUBLICATIONS

Shi, S. et al., "Dual drugs (microRNA-34a and paclitaxel)-loaded functional solid lipid nanoparticles for synergistic cancer cell suppression" Journal of Controlled Release, 2014, vol. 194, pp. 228-237.
Silva, A.C., et al., "Lipid Nanoparticles for the Delivery of Biopharmaceuticals", Current Pharmaceutical Biotechnology, 2015, vol. 16, No. 4, pp. 291-302.
Written Opinion of the International Search Authority for International Application No. PCT/ES2017/070205 filed on Apr. 4, 2017; dated Jun. 29, 2017; 6 pages.
Wu, Sherry Y., et al. "2'f-OMe-phosphorodithioate modified siRNAs show increased loading into the RISC complex and enhanced anti-tumour activity" Nat Commun, 2014, 5: 3459.

\* cited by examiner

VEHICLES FOR THE TRANSFECTION OF MIRNAS

TECHNICAL FIELD

The present disclosure relates to new systems comprising miRNAs for their application in the pharmaceutical, cosmetic or nutritional fields, among others. These systems allow for the most efficient administration of different miRNAs, for example, in applications for the treatment of cancer.

BACKGROUND

MicroRNAs, also commonly called miRNAs, are short sequences of RNA that have the ability to interfere in cellular processes. This ability has aroused interest in their potential for medical, cosmetic or nutritional applications, among others. It has been possible to verify the potential of many of these miRNAs through biological assays, and to date, approximately a thousand of these natural substances with potential in various applications have been identified.

So far, the main problem in their use is their short life when they are administered. MiRNAs are especially sensitive to attack by exonucleases and have a half-life of minutes in biological medium. This has sparked interest in the search for administration means that allow the miRNAs to be transported efficiently, avoiding their rapid degradation in vivo.

One of the first strategies contemplated was the structural modification of miRNAs. One of the most widespread variations has been the modification of the ribose 2'—OH group (Wu S Y, Yang X, Gharpure K M, Hatakeyama H, Egli M, et al. (2014) 2'-OMe-phosphorodithioate-modified siRNAs show increased loading into the RISC complex and enhanced anti-tumour activity. Nat Commun 5: 3459). Examples of these modifications are the substitution in this position by 2'-fluoro, 2'-O-methyl or 2'-O-methoxymethyl, just to mention a few examples.

Another strategy followed has been the use of viral vectors, for example, lentivirus or adenovirus, as explained in Kasar S, Salerno E, Yuan Y, Underbayev C, Vollenweider D, et al. (2012) Systemic in vivo lentiviral delivery of miR-15a/16 reduces malignancy in the NZB de novo mouse model of chronic lymphocytic leukemia. *Genes Immun* 13: 109-119; or in Brandt M R, Kirste A G, Pozzuto T, Schubert S, Kandolf R, et al. (2013) Adenovirus vector-mediated RNA interference for the inhibition of human parvovirus B19 replication. *Virus Res* 176: 155-160. However, despite the fact that they have been genetically modified to eliminate their virulent burden, the safety of these vectors always arouses concern.

So far, it is possibly in the field of oncology that miRNAs have received most attention. This interest was generated by the discovery that miRNAs are deregulated in cancerous tissues and the tissues surrounding them, and in the ability of miRNAs to regulate multiple genes (for example, siRNAs are specific and allow action on a single gene), since they can bind to multiple messenger RNAs (mRNA) (GARZON, R., MARCUCCI, G. and CROCE, CM, 2010. Targeting microRNAs in cancer: rationale, strategies and challenges. Nature reviews. Drug discovery, 9(10), pp. 775-789).

An example is the case of colorectal cancer and liver metastasis, one of its most frequent regions where metastasis develops. Liver sinusoidal endothelial cells (LSECs) play a key role in the development and regulation of liver metastasis. It has been found that some miRNAs (miR-20a, miR-29 and miR-652) are deregulated in the LSECs, and the recovery of their normal levels appears as a promising therapeutic alternative.

In view of the potential of miRNAs and their difficulties on administration, the use of non-viral vectors such as liposomes, peptides, antibodies and other ligands, such as chitosan, has been tried. Thus, improvement in the transfection of different miRNAs with the usual agents, such as those of the Lipofectamine® family (DOTAP, DOTMA or DOPE) or Smarticles® (amphoteric derivatives) has been sought. For example, miR-34a is now in phases of clinical trials in the form of Smarticles® liposomes for the treatment of liver cancer, and miR-16 in the form of EnGeneIC nanoparticles (minicell; EP2386640) for the treatment of malignant pleural mesothelioma. This situation differs from that of drugs based on siRNAs, another different family of RNAs that have double chain, which are not coming across so many problems in the search for suitable vehicles for their transfection, and for which there are already many clinical trials in progress.

Given the recent interest aroused by miRNAs as therapeutic agents, there is a need to find and develop new vehicles for more effective administration (LAM, J K, CHOW, M Y, ZHANG, Y. and LEUNG, S W, 2015. siRNA Versus miRNA as Therapeutics for Gene Silencing. *Molecular therapy. Nucleic acids*, 4, pp. e252). However, in the case of miRNAs, efforts are proving particularly difficult since they are molecules of hydrophilic nature, high molecular weight and negative charge, which prevent their passage through the cell membrane.

The use of non-viral vectors mentioned above reduces these problems; however, especially in the case of nanometric systems, it creates other difficulties. The reticuloendothelial system (RES) quickly absorbs nanometric systems, and is the cause of poor stability in vivo (and therefore, poor efficacy) of many of them (RINKENAUER, A C, PRESS, A T, RAASCH, M., PIETSCH, C., SCHWEIZER, S., SCHWORER, S., RUDOLPH, K. L., MOSIG, A., BAUER, M., TRAEGER, A., and SCHUBERT, U. S., 2015. Comparison of the uptake of methacrylate-based nanoparticles in static and dynamic in vitro systems as well as in vivo. Journal of controlled release: official journal of the Controlled Release Society, 216, pp. 158-168; SADAUSKAS, E., WALLIN, H., STOLTENBERG, M., VOGEL, U., DOERING, P., LARSEN, A., and DANSCHER, G., 2007. Kupffer cells are central in the removal of nanoparticles from the organism. *Particle and fibre toxicology*, 4, pp. 10). RES comprises phagocytic cells such as monocytes or macrophages, for example, Kupffer cells. Although it is generally accepted that there is a correlation between the positively charged surface of the nanoparticle and lower absorption by phagocytic cells, it is not known exactly which factors influence this absorption, which makes it difficult to predict the type of nanometric systems that will have adequate stability in vivo.

The development of vehicles with improved properties for the administration of miRNAs is therefore of great interest.

BRIEF SUMMARY

The present disclosure solves the aforementioned problems described above, improving the stability of miRNAs in vivo. Researchers have been able to verify that the systems of the present disclosure surprisingly improve the in vivo transport of miRNAs, and their efficiency is surprisingly increased. It has been proven that it prevents its degradation by the RES, and in particular prevents phagocytosis by the Kupffer cells.

Therefore, a first aspect of the disclosure is a nanoparticle comprising (i) between 60% and 99% by weight, based on the total weight of the nanoparticle, of a sorbitan ester; (ii) a positively charged substance; and (iii) a miRNA.

The stability of these systems and the improvement in the transfection of miRNAs they provide make the nanoparticles of the disclosure suitable for, for example, applications in the field of pharmacy, cosmetics or nutrition.

An additional aspect is the use of a nanoparticle of the disclosure for preparing a drug. A nanoparticle of the disclosure for use as a drug is also an additional aspect.

A further aspect is the use of a nanoparticle of the disclosure for preparing a drug for the treatment of an indication that is selected from the group consisting of cancer, diabetes and neurodegenerative diseases. In addition, an aspect is a nanoparticle of the disclosure for use in the treatment of an indication that is selected from the group consisting of cancer, diabetes and neurodegenerative diseases.

Another advantage of the disclosure is that the nanoparticles are easy to prepare, and the incorporation of the miRNAs can be performed simultaneously with the formation of the nanoparticle itself or at a later step of incubation, depending on the nature of the components, thus providing flexibility in its preparation. Thus, a further aspect of the disclosure is a method for preparing a nanoparticle of the disclosure comprising (i) the step of adding an organic solution comprising an organic solvent and a sorbitan ester on an aqueous solution; wherein said organic solution or said aqueous solution or both comprise a positively charged substance; and (ii) the step of evaporating organic solvent and water; and (iii) the optional step of incubating the nanoparticle resulting from step (ii) in the presence of other substances; wherein a miRNA is incorporated (a) during step (i) as part of the aqueous solution, (b) in the incubation step (iii), or in both steps (i) and (ii).

A further aspect of the disclosure is a pharmaceutical composition comprising the nanoparticle of the disclosure and a pharmaceutically acceptable excipient.

BRIEF DESCRIPTION OF THE DRAWINGS

FIG. 5: TEM images of nanoparticles. 1) Blank SP-OA-CS nanoparticles, 2) Nanoparticles loaded with pEGFP, 3) nanoparticles loaded with miR-20a.

FIG. 8: The Western blot transfer analysis of ARHGAP1 and E2F1 validates the role of miR-20a in the expression pattern of two of the predicted targets. Analyses were performed in 5 different conditions: i) LSEC from healthy livers, ii) LSEC from livers colonised by the tumour, iii) LSEC from livers colonised by the tumour and treated with the transfection vehicle Mirus, iv) LSEC from livers colonised by the tumour and transfected with control non-specific miRNA and v) LSEC from livers colonised by the tumour and transfected with miR-20a.

DETAILED DESCRIPTION

Definitions

Figure 1:
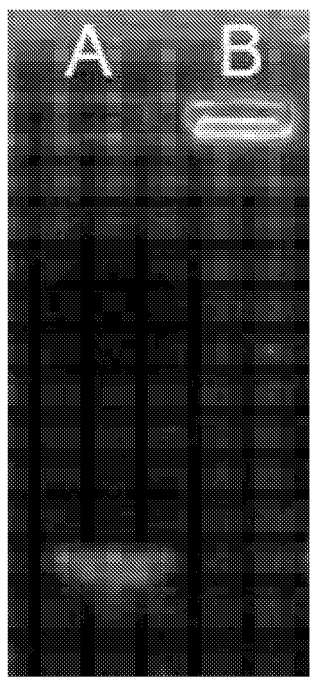
FIG. 1. Electrophoresis gel confirming the existence of an effective association between a miRNA and the nanoparticles prepared in Example 1. A: band corresponding to free miR-20a (5 µg/mL). B: band in which free miR-20a is not observed, corresponding to SP80-OA-CS-miR-20a (50 µg/mL miR-20a).

The formula [sorbitan ester]-[positively charged substance] is used for the nomenclature of the nanoparticles of the disclosure. If the nanoparticle has further components, for example, a negatively charged substance, it follows separated by a hyphen. In some cases, the name of the miRNA used is indicated at the end. Also, the following abbreviations are used:

SP80: means Span-80®. Span-80® is a substance that results from esterifying sorbitan with cis-9-octadecenoic acid (commonly known as oleic acid), i.e., a molecule with the following formula:

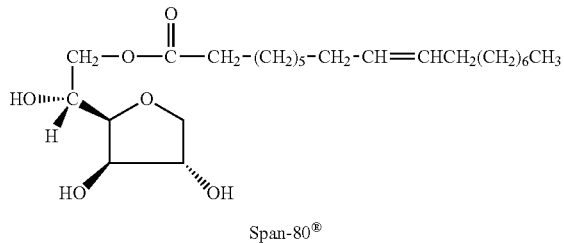

Span-80®

OA: oleylamine, i.e. (Z)-octalec-9-enylamine.

CS: chondroitin sulphate. Its structure and properties are explained below in greater detail.

HA: hyaluronic acid. Its structure and properties are explained below in greater detail.

In this way, for example, a nanoparticle that is abbreviated SP80-OA-HA-miR-20α, will be one that incorporates Span-80®, oleylamine, hyaluronic acid and miR-20α, prepared in accordance with the methods described herein.

In the present document, standard nomenclature for miRNAs has been used. The prefix "miR-" has been used followed by a hyphen and a number. According to the standard nomenclature, the prefix "miR" with upper case "R" applies to mature miRNAs, while the prefix "mir-" with lower case "r" usually applies to pre-miRNAs, and the prefix "MIR" for the gene encoding them. For the purposes of the present disclosure, the prefix "miR-" includes all of them, the mature miRNAs, the pre-miRNAs and the genes encoding them. After the number, some miRNAs incorporate a letter allowing distinguishing miRNAs with very similar sequences.

"Alkyl" means a straight or branched hydrocarbon chain containing no unsaturation, from 1 to 40 carbon atoms unless otherwise indicated, optionally substituted with one, two or three substituents selected from —ORb, —SRb, —NRaRb, —C(O)Rb, —CO$_2$Rb, —C(O)NRaRb, —NRaC(O)Rb, NRaC(O)ORb, —NRaC(O)NRaRb, —CF$_3$, —OCF$_3$; where Ra and Rb are independently selected from hydrogen, $C_1$-$C_6$ alkyl, $C_2$-$C_6$ alkenyl, and $C_2$-$C_6$ alkynyl.

"Alkenyl" means a straight or branched hydrocarbon chain containing at least one double bond, from 2 to 40 carbon atoms unless otherwise indicated, optionally substituted with one, two or three substituents selected from —ORb, —SRb, —NRaRb, —C(O)Rb, —CO$_2$Rb, —C(O)NRaRb, —NRaC(O)Rb, —NRaC(O)ORb, —NRaC(O)NRaRb, —CF$_3$, —OCF$_3$; where Ra and Rb are independently selected from hydrogen, $C_1$-$C_6$ alkyl, $C_2$-$C_6$ alkenyl, and $C_2$-$C_6$ alkynyl.

"Alkynyl" means a straight or branched hydrocarbon chain containing at least one triple bond, from 2 to 40 carbon atoms unless otherwise indicated, optionally substituted with one, two or three substituents selected from —ORb, —SRb, —NRaRb, —C(O)Rb, —CO$_2$Rb, —C(O)NRaRb, —NRaC(O)Rb, —NRaC(O)ORb, —NRaC(O)NRaRb, —CF$_3$, —OCF$_3$; wherein Ra and Rb are independently selected from hydrogen, $C_1$-$C_6$ alkyl, $C_2$-$C_6$ alkenyl, and $C_2$-$C_6$ alkynyl.

Unless otherwise specified, the percentages by weight indicated in this text are calculated based on the addition of all the components added to the mixture in the formation of the nanoparticle, with the exception of the solvents. For example, for a nanoparticle SP80-OA-HA-miR-20α the percentage by weight of SP80 will be the grams of SP80 added for preparing the nanoparticle, multiplied by one hundred, and divided by the addition of grams of SP80, OA, HA and miR-20α added for preparing the nanoparticle. When the particle "one" is used, it should be understood as "at least one" or "one or more". For example, "a miRNA" indicates that the number of miRNAs present is at least 1, but that mixtures of 2 or more miRNAs may exist.

Components of the Nanoparticles of the Disclosure

The nanoparticles of the disclosure comprise sorbitan esters. Sorbitan is constituted by a mixture of cyclic sorbitol anhydrides, such as, for example, 1,4-anhydrosorbitol, 1,5-anhydrosorbitol and 1,4,3,6-dianhydrosorbitol. Sorbitan esters are considered non-ionic surfactants because they contain two localised regions, one of them is hydrophilic and the other is hydrophobic.

"Sorbitan esters" means sorbitan esterified derivatives where the ester groups have a substituent selected from alkyl, alkenyl, and alkynyl. Sorbitan esters include derivatives in which one, two, three or four hydroxyl groups are esterified, and even include esterified derivatives in which one ester molecule is present for every two sorbitan molecules (in which case they are named with the prefix "sesqui-"). Thus, for example, sorbitan monooleate is the sorbitan ester resulting from the esterification of a hydroxyl group with oleic acid; sorbitan trioleate is the sorbitan ester resulting from the esterification of three sorbitan hydroxyl groups with oleic acid. There are many different types of sorbitan esters based on the number of esterified hydroxyls, the structure of the ester, the anhydrosorbitol mixture, and other factors. The person skilled in the art can choose between different types within the scope of the disclosure and is not limited to a specific type.

Commonly used sorbitan esters are, for example, those available in the market under the name Span® (without polyoxyethylene blocks) or Tween® (with polyoxyethylene blocks). To mention a few examples, common sorbitan esters of the Span® family may be Span-80® (sorbitan monooleate), Span-20® (sorbitan monolaurate), Span-40® (sorbitan monopalmitate), Span-65 (sorbitan tristearate), or Span-85® (sorbitan trioleate). Common sorbitan esters of the Tween® families are Tween® 20 (polyoxyethylene sorbitan monolaurate), Tween® 40 (polyoxyethylene sorbitan monopalmitate), Tween® 60 (polyoxyethylene sorbitan monostearate) or Tween® 80 (polyoxyethylene sorbitan monooleate).

The formation of the nanoparticles of the disclosure may comprise mixtures of two or more different sorbitan esters, such as a mixture of a sorbitan ester without polyoxyethylene blocks with another sorbitan ester with polyoxyethylene blocks. In the preparation of the nanoparticles of the disclosure the person skilled in the art may therefore choose various sorbitan esters to combine with the positively charged substance, and by way of example, they can be selected from the group consisting of sorbitan monooleate, sorbitan dioleate, sorbitan trioleate, sorbitan sesquioleate, sorbitan monolaurate, sorbitan dilaurate, sorbitan trilaurate, sorbitan sesquilaurate, sorbitan monostearate, sorbitan distearate, sorbitan tristearate, sorbitan sesquistearate, sorbitan monopalmitate, sorbitan dipalmitate, sorbitan tripalmitate, sorbitan sesquipalmitate and combinations thereof.

Taking into account that said sorbitan esters optionally comprise polyoxyethylene blocks, the sorbitan ester used in the nanoparticles of the disclosure can be a compound of formula I

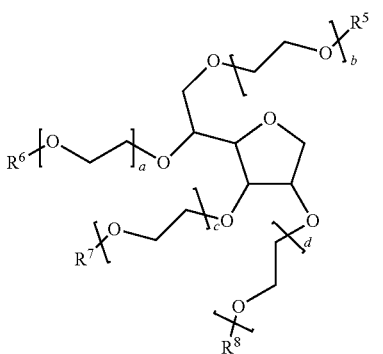

Formula I where
each of $R^5$, $R^6$, $R^7$ and $R^8$ is independently selected from the group consisting of —H, —(C=O)—$C_1$-$C_{40}$ alkyl, —(C=O)—$C_2$-$C_{40}$ alkenyl, —(C=O)—$C_2$-$C_{40}$ alkynyl, provided that at least one of $R^5$, $R^6$, $R^7$, and $R^8$ is not —H; and each of a, b, c and d is independently a number between 0 and 100.

The most common ones are those commercially available and usually correspond to a linear alkyl comprising between 2 and 20 carbon atoms, for example, one with 9, 11, 13, 15 or 17 carbon atoms, or a linear alkenyl group comprising between 4 and 25 carbon atoms. Thus, an example can be an alkenyl group of formula —$(CH_2)_n$—CH=CH—$(CH_2)_m$—$CH_3$, where n is an integer between 1 and 10, and m is an integer between 1 and 10. One commonly used is one in which n is 7 and m is 7, corresponding to oleic acid. As can be seen, the polyoxyethylene blocks are optional, and each of a, b, c and d can be 0. In the case of including said polyoxyethylene blocks, the addition of a, b, c and d can be, for example, between 10 and 50 or between 10 and 30 or between 15 and 30. For example, in the case of Tween® 80 (polyoxyethylene sorbitan monooleate) a, b, c and d add up to 20.

According to a preferred embodiment, $R^6$, $R^7$ and $R^8$ are —H. That is, it is a sorbitan monoester, for example, one that is selected from the group consisting of sorbitan monooleate, sorbitan monolaurate, sorbitan monostearate, sorbitan monopalmitate, and combinations thereof. This group of sorbitan monoesters can be represented by formula II

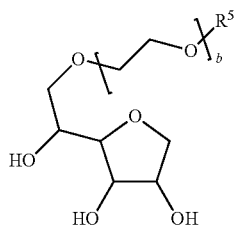

Formula II where
$R^5$ is selected from the group consisting of —(C=O)—$C_1$-$C_{40}$ alkyl and —(C=O)—$C_2$-$C_{40}$ alkenyl; and
b is a number between 0 and 100, preferably 0.

Once again, one wherein $R^5$ is an alkenyl of the formula —$(CH_2)_n$—CH=CH—$(CH_2)_m$—$CH_3$ is preferred where n is an integer between 1 and 10, and m is an integer between 1 and 10.

The proportion of sorbitan esters in the nanoparticles is between 60% and 99% by weight based on the total weight of the nanoparticle. Typical proportions of sorbitan esters are between 80% and 98% by weight based on the total weight of the nanoparticle, for example, between 85% and 95%. The proportion of the sorbitan esters is usually greater than 87% by weight based on the total weight of the nanoparticle.

Another essential component of the disclosure is the inclusion of a positively charged substance. In the context of the present disclosure, "positively charged substance" means a molecule with positive electric charge. In the field of the present disclosure, these substances are used to modulate the properties of the particles formed, and a wide variety of them is available to the person skilled in the art. These substances are discussed extensively in numerous reference books, for example, in "Dekker Encyclopaedia of Nanoscience and Nanotechnology, Volume 4", James A. Schwarz, Cristian I. Contescu, Karol Putyera, Publisher: Marcel Dekker, 2004, or in "Encyclopaedia of Polymer Science and Technology, Concise", Herman F. Mark, third edition, Publisher: Wiley, 2007. Non-limiting examples are ammonium salts, cationic polymers and fatty or lipophilic amines.

The cationic polymer can be selected from the group consisting of protamine, polyglutamic acid, cationised dextran, cationised pullulan, polyamino acids, cationised proteins, and salts thereof. The polyamino acids are another family of positively charged substances which can be used in the nanoparticles of the disclosure and which can be selected from the group consisting of polylysine and polyarginine. The cationised proteins may be selected from the group consisting of gelatin, albumin, collagen, atelocollagen, and cationised derivatives thereof.

The ammonium salts may be substances comprising an ammonium or amine group attached to one, two or three moieties, which are independently selected from the group consisting of $C_1$-$C_{40}$ alkyl, $C_2$-$C_{40}$ alkenyl, $C_2$-$C_{40}$ alkynyl, for example, selected from the group consisting of cetyl trimethyl ammonium bromide (CTAB) and benzalkonium chloride (BZC). The fatty amine may be oleylamine. Positively charged substances suitable for the present disclosure may be ammonium salts or fatty amines, for example CTAB, BZC, oleylamine or mixtures thereof. Thus, said positively charged substance can have the formula $(R^{10})_p(R^{11})(R^{12})NR^9$, where
each of $R^{10}$, $R^{11}$, and $R^{12}$ is independently selected from the group consisting of
—H, $C_1$-$C_4$ alkyl, $C_2$-$C_4$ alkenyl, $C_2$-$C_4$ alkynyl, and $C_7$-$C_{15}$ phenylalkyl; $R^9$ is selected from the group consisting of $C_1$-$C_{40}$ alkyl, $C_2$-$C_{40}$ alkenyl, $C_2$-$C_{40}$ alkynyl;
p is 0 or 1;
and where it also comprises a counter-anion when p is 1. Which is the counter-anion is not critical and may be, for example, a halogenide (F$^-$, Cl$^-$, Br$^-$, or I$^-$).

The negatively charged substance may be added in proportions ranging from 1% to 39% by weight based on the total weight of the nanoparticle. Preferred amounts range between 2% and 20%, typically between 3% and 12% or between 2% and 9% or between 3% and 8% by weight based on the total weight of the nanoparticle.

An optional component of the nanoparticles of the disclosure is a negatively charged substance. These substances are known to the person skilled in the art and, for the present disclosure, those capable of forming a coating layer on the nanoparticle are preferred. According to the present disclosure, the family of negatively charged substances may be an anionic polymer, anionic polymer meaning a polymer with a negative charge.

Researchers have found that the incorporation of one or more negatively charged substances provides surprising advantages. Contrary to what might be expected from a system with a negatively charged surface, they support the attacks of the RES (no phagocytosis by the Kupffer cells was observed) and the nanoparticles improve the transfection ability of the transported miRNA. This is contrary to the observations described in the literature in which a positive correlation is established between the negative charge and increased phagocytosis by Kupffer cells.

The anionic polymers are preferably polysaccharides. A great variety of these polysaccharides is available to the person skilled in the art, and they are frequently used in this field. A preferred variety are those containing a carboxyl group (—COOH) or sulphate (—SO3H) in the repeating monomer. Particularly suitable for the present disclosure have been shown those polysaccharides having at least one glucuronic acid in the repeating structure. For example, said negatively charged substance may comprise a polysaccharide whose repeating unit has the formula [XY—(Z)$_n$] where n is 0 or 1; X, Y, and Z are each independently selected from the group consisting of monosaccharides, disaccharides and polysaccharides; with the proviso that at least one of X, Y, and Z comprises an acid sugar and wherein the X, Y, and Z groups are linked together through —O-glycosidic bonds. According to an embodiment of the disclosure, said acid sugar is selected from the group consisting of aldonic acids, ulosonic acids, uronic acids, aldaric acids and mixtures thereof. For example, Y can comprise an acid sugar, for example, an uronic acid. A non-limiting example of said uranic acid may be one of formula III

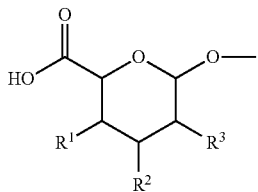

Formula III where
each of $R^1$, $R^2$ and $R^3$ is independently selected from the group consisting of —H, —OH, —O—, N(H)—$R^4$, and —O—SO$_3$, provided that at least one of $R^1$, $R^2$, and $R^3$ is —O—,
where the —O— form the glycosidic bonds, and
where $R^4$ is selected from the group consisting of $C_1$-$C_4$ alkyl, $C_2$-$C_4$ alkenyl, $C_2$-$C_4$ alkynyl, —(C═O)—$C_1$-$C_4$ alkyl, —(C═O)—$C_2$-$C_4$ alkenyl, —(C═O)—$C_2$-$C_4$ alkynyl. Non-limiting examples of negatively charged substances having this formula are selected from the group consisting of hyaluronic acid, chondroitin sulphate and xanthan gum.

The negatively charged substances that can be incorporated into the nanoparticles of the present disclosure can also be those selected from the group consisting of hyaluronic acid, colominic acid, polysialic acid, chondroitin, keratan, dextrans, heparin, carrageenans, furcellarans, alginates, agar, glucomannan, gellan gum, locust bean gum, guar gum, tragacanth gum, arabic gum, xanthan gum, karaya gum, pectins, celluloses, starches, and salts, fragments, derivatives and mixtures thereof.

Hyaluronan is a linear polymer comprising the repetition of a disaccharide structure formed by the alternating addition of D-glucuronic acid and D-N-acetylglucosamine, linked alternating beta-1,4- and beta-1,3-glycosidic bonds. In the context of the present disclosure, hyaluronic acid with a wide range of molecular weights can be used. High molecular weight hyaluronic acid is commercially available, while lower molecular weight hyaluronic acid can be obtained by fragmentation of high molecular weight hyaluronic acid, using, for example, a hyaluronidase enzyme. The term "hyaluronic, hyaluronic acid, hyaluronan" as used in the present disclosure includes either hyaluronic acid or a conjugate base thereof (hyaluronate). This conjugate base can be an alkaline salt of hyaluronic acid including inorganic salts such as, for example, sodium, potassium, calcium, ammonium, magnesium, aluminium, and lithium salts, organic salts such as salts of basic amino acids at neutral pH, said salts being preferably pharmaceutically acceptable. In a preferred embodiment of the disclosure, the alkaline salt is sodium salt of hyaluronic acid.

The family of polysialic acids, a term that includes colominic acid, is made up of linear polymers formed by residues of N-acetylneuraminic acid (Neu5Ac, also known as sialic acid), a natural constituent of cells and tissues, linked by α-(2→8) glycosidic bonds. Each residue of N-acetylneuraminic acid has a carboxyl group responsible for the negative charge of the colominic acid. It is a biocompatible and biodegradable, non-immunogenic, material whose degradation products are not toxic (Gregoriadis G et al. Cell. Mol. Life Sci. 2000, 57, 1964-1969).

Dextran sulphate is a complex glucan (polysaccharide) consisting of units of glucose molecules, each of which contains approximately two sulphate groups. Dextran sulphate is prepared by dextran sulphation and subsequent purification by well-known procedures known to a person skilled in the art.

Heparin is a substance of natural origin from the family of glycosaminoglycans whose chemical structure comprises the repetition of disaccharide monomeric units of 2-O-sulfo-L-iduronic acid and 2-deoxy-2-sulfamido-D-glucopyranosyl-6-O-sulphate. In the context of the present disclosure, it is possible to use both fractionated and unfractionated heparin. Traditional or unfractionated heparin is clearly distinguished from fractionated or low molecular weight heparin. The first one is a natural substance present in all vertebrates. Both types of heparin can be used in the form of a free base or in the form of a salt, such as, for example, their sodium or calcium salt. Fractionated or low molecular weight heparin is produced by chemical or enzymatic depolymerisation of conventional heparins. Examples of this type of heparins are enoxaparin, parnaparin, dalteparin, and nadroparin, as well as salts thereof, such as sodium and calcium salts. Heparin derivatives can also be used in the composition of the nanoparticular systems of the present disclosure. These derivatives are known in the state of the art and originate as a consequence of the reactivity of the different functional groups present in the molecule.

Thus, N-acetylated, O-decarboxylated, oxidised or reduced heparins are widely known.

Chondroitin sulphate is a sulphated glycosaminoglycan (GAG) made up of a chain of alternating sugars. It is normally found bound to proteins as part of a proteoglycan. In the context of the present disclosure, the term "chondroitin sulphate" includes all its different isomers and derivatives, as well as combinations thereof. For example, it is selected from the following substances and combinations thereof, summarised in formula IV

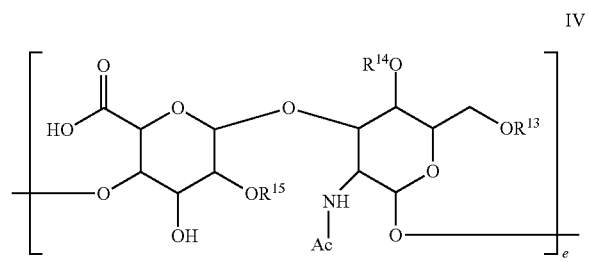

chondroitin sulphate A which is sulphated predominantly in the carbon 4 of the sugar N-acetylgalactosamine (GalNAc) and which is also known as 4-chondroitin sulphate ($R^{13}$=H, $R^{14}$=$SO_3H$, and $R^{15}$=H)

chondroitin sulphate B which is also referred to as dermatan sulphate. This substance is made up of linear repeating units containing N-acetylgalactosamine and either L-iduronic acid or glucuronic acid, and each disaccharide can be sulphated once or sulphated twice. It is present mainly in the skin, but it is also found in blood vessels, heart valves, tendons and lungs.

chondroitin sulphate C which is sulphated predominantly in the carbon 6 of the sugar GalNAc and which is also known as 6-chondroitin sulphate ($R^{13}$=$SO_3H$, $R^{14}$=H, and $R^{15}$=H);

chondroitin sulphate D which is sulphated predominantly in carbon 2 of glucuronic acid and in carbon 6 of the sugar GalNAc and is also known as 2,6-chondroitin sulphate ($R^{13}$=$SO_3H$, $R^{14}$=H, and $R^{15}$=$SO_3H$);

chondroitin sulphate E which is sulphated predominantly in the carbons 4 and 6 of the sugar GalNAc and is also known as 2,6-chondroitin sulphate ($R^{13}$=$SO_3H$, $R^{14}$=$SO_3H$, and $R^{15}$=H); and where "e" represents the number of repetitions of the monomer, that is, its polymerisation level.

The term "chondroitin sulphate" also includes organic and inorganic salts thereof. Generally, such salts are prepared, for example, by reaction of the basic form of this compound with a stoichiometric amount of the appropriate acid in water or in an organic solvent or in a mixture of the two. Generally, non-aqueous media such as ether, ethyl acetate, ethanol, isopropanol or acetonitrile are preferred. Examples of inorganic salts include sodium, potassium, calcium, ammonium, magnesium, aluminium, and lithium salts, and organic salts include, for example, ethylenediamine, ethanolamine, N, N-dialkylene-ethanolamine, triethanolamine, basic glucamine and basic amino acid salts. Preferably, the salts are pharmaceutically acceptable.

Keratan sulphate is a sulphated glycosaminoglycan similar to chondroitin sulphate in which the sulphate group is in the glucuronic acid. Specifically, it is constituted by galactose and GlcNAc-6-sulphate, linked by a β-1,4 bond.

Carrageenin or carrageenan is formed by units of galactose and/or of sulphated or unsulphated anhydrogalactose linked by alternating bonds -1,3 and -1,4. Depending on the sulphation level, the positions of the sulphate groups, and the presence of anhydrogalactose groups, various types of carrageenan are distinguished, all falling within the scope of the present disclosure.

Glucomannan is a water-soluble polysaccharide of natural origin. The chemical structure of this compound consists of a linear polymer chain with a small proportion of branches. Specifically, it consists of units of D-mannose and D-glucose linked by -1,4 bonds in a ratio of 1.6:1, respectively. In a particular embodiment of the disclosure, the glucomannan used is a negatively charged glucomannan derivative selected from the carboxymethyl and dicarboxy-glucomannan phosphorylated derivatives.

Gellan gum is a water-soluble polysaccharide of natural origin. The chemical structure of this compound consists of a polymer chain formed by units of α-L-rhamnosium, β-D-glucuronic acid and two units of β-D-glucose. The polymer may be in partially acetylated form. Depending on its acetylation level, gellan gum provides gels with different mechanical properties. In the context of the present disclosure, the term "gellan gum" includes all its different derivatives, as well as combinations thereof. Without wishing to be limited by the theory, we think that the nanoparticles of the disclosure are solid homogeneous structures in which the miRNAs are adsorbed. This is contrary to the systems used for transporting miRNAs that have been used so far. As already mentioned above, those that are now being used to carry out clinical trials of miRNAs use liposomes or vesicles, that is, lipid bilayer structures that enclose an aqueous phase inside them. MiRNAs are bound to the solid structure formed by the sorbitol esters and the positively charged substance.

The average size of the nanoparticles of the disclosure is between 1 and 999 nanometres, and they may have a negative or positive potential, depending on the added components, for example, whether or not they comprise a negatively charged substance, or the concentration of the added miRNA(s). According to a preferred embodiment, the nanoparticle of the disclosure has a positive potential comprised between +1 and +100 mV. According to another preferred embodiment, the nanoparticle of the disclosure has a negative potential comprised between −25 and −40 mV.

The nanoparticles of the disclosure can include other auxiliary substances, for example, an ethylene oxide derivative, a compound in which a —$CH_2CH_2O$— unit is repeated. Said ethylene oxide derivative can be a compound of formula $R^{16}O[CH_2$—$CH_2$—$O]_f$—$C(H)(R^{17})(R^{18})$, where $R^{17}$ is a carbonyl or hydrogen group; $R^{18}$ is an alkyl, alkenyl or alkynyl group, of between 2 to 24 carbon atoms; $R^{16}$ is hydrogen or an alkyl group of between 1 to 6 carbon atoms; f is a value between 1 and 100, for example, between 1 and 50, or between 1 and 24. Examples of ethylene oxide derivatives, without being limited thereto, are polyethylene glycol dodecyl ether (Brij 30), polyethylene glycol hexadecyl ether (Brij 56), polyethylene glycol 2-octadecyl ether (Brij 72), polyethylene glycol 8-octadecyl ether (Brij 78), polyethylene glycol 8-stearate (Myrj 45), 2-hydroxyethyl octadecanoate (Myrj 52), and ethylene glycol monostearate.

The ethylene oxide derivatives may be incorporated in proportions ranging between 0.1% and 20% by weight based on the total weight of the nanoparticle. Depending on the applications, the proportions may vary and be of, for example, between 0.1% and 15%, or between 5% and 15% or between 7% and 13%, by weight based on the total weight of the nanoparticle.

Applications and miRNAs

The other essential component of the nanoparticles of the disclosure is a miRNA or a mixture of miRNAs, which are usually found in proportions below 25% by weight based on the total weight of the nanoparticle. The proportion in which they are found in each case can be adjusted and can be, for example, between 0.01 and 10% or between 0.2% and 3% by weight based on the total weight of the nanoparticle. The miRNAs that are used in the nanoparticles of the disclosure are RNA molecules that typically comprise between 5 and 30 bases or between 15 and 25 bases.

The miRNAs, and therefore also the nanoparticles of the disclosure, have multiple applications, for example, in the pharmaceutical, cosmetic or nutrition field. Thus, for example, the therapeutic application of various miRNAs in fields such as cancer (miRNA-20a, miR-29, miR-652 miR-34a, miR-16), diabetes or neurodegenerative diseases is currently being studied. One of the fields in which the use of miRNAs has been most developed is that of cancer. Thus, a preferred embodiment is the nanoparticles of the disclosure for use in the treatment of a cancer that is selected from the group consisting of colorectal cancer, malignant pleural mesothelioma, liver cancer, pancreatic cancer, colon cancer, and liver and lung metastases.

On the other hand, the proteins ARHGAP1 and E2F1 have been identified as targets of miR-20a, therefore, the use of the nanoparticles of the disclosure for preparing a drug for the treatment of a disease mediated by ARHGAP1 and/or E2F1 is another aspect of the disclosure. Overexpression of E2F1 is related to glioblastoma, pancreatic cancer, melanoma and testicular cancer and that of ARHGAP to breast cancer. Therefore, the particles of the disclosure are also useful for preparing a drug for the treatment of a condition that is selected from the group consisting of glioblastoma, pancreatic cancer, melanoma, testicular cancer and breast cancer.

The term "treatment" or "treating" herein means administering the nanoparticles of the disclosure to prevent, reduce or eliminate one or more of the symptoms or causes or effects (metastasis) of a disease or condition. It also covers the prevention, reduction or elimination of the sequelae of said disease or condition, or of the secondary or adverse effects caused by another drug used. It also covers the administration to maintain health in subjects at risk of suffering from this disease. The term "reduce" means any improvement in the patient's situation, measured by either subjective parameters (for example, patient perception) or objective parameters (measurement of physiological, biochemical, histopathological, microbiological-analytical parameters).

For example, the nanoparticles of the disclosure for use in the treatment of liver metastasis is an embodiment of the disclosure, and it has been found that they allow to reduce or eliminate the metastasis and the effects of said metathesis in liver that often accompanies colorectal cancer, which also constitutes an embodiment of the disclosure. In one embodiment, the nanoparticles of the disclosure comprise miR-20a, miR-29, miR-652 or mixtures thereof, preferably miRNA-20a, for use in the treatment of colorectal cancer and/or its associated liver metastasis.

Another aspect of the disclosure is a method for the treatment of an individual in need of treatment comprising the administration of a therapeutically effective amount of nanoparticles of the disclosure. In the sense used in this description, "therapeutically effective amount" means the amount of active ingredient calculated to produce the desired effect and will generally be determined, among other reasons, by the characteristics of the active ingredient used and the therapeutic effect to be obtained. In a particular embodiment, the dose of active ingredient administered to a subject for the treatment or prophylaxis of the aforementioned conditions is in the range of $10^{-10}$ to $10^{10}$ mg/kg of body weight, normally between $10^{-3}$ and $10^3$ mg/kg or between $10^{-2}$ and 50 mg/kg of body weight.

Thus, the nanoparticles of the disclosure can form pharmaceutical compositions together with a pharmaceutically acceptable excipient. In fact, it is preferred that all components are pharmaceutically acceptable. The term "pharmaceutically acceptable" means molecular entities and compositions that are physiologically tolerable and do not normally produce an undesired allergic reaction or the like, such as gastric discomfort, dizziness and the like, when administered to humans. Preferably, as used herein, the term "pharmaceutically acceptable" means approved by a regulatory agency of the federal or state government or listed in the US Pharmacopoeia or another pharmacopoeia generally recognised for use in animals and more particularly in humans.

The term "excipient" means a diluent, adjuvant, or vehicle with which the nanoparticles of the disclosure are administered. They are substances that, for example, are added to the active ingredients or their associations to serve as a vehicle, to enable their preparation and stability, to modify their organoleptic properties or to determine the physicochemical properties of the drug and its bioavailability. Such pharmaceutical vehicles can be sterile liquids, such as water or oils, including those of petroleum, animal, vegetable or synthetic origin, such as peanut oil, soybean oil, mineral oil, sesame oil and the like. Water or saline aqueous solutions, and dextrose and glycerol or glucose and glycerol aqueous solutions are preferably used as vehicles, particularly for injectable solutions. Suitable pharmaceutical vehicles are described in "Remington's Pharmaceutical Sciences" by E. W. Martin.

The pharmaceutical composition or drug may be in any form suitable for administration to humans and/or animals, preferably humans, including infants, children and adults and may be prepared by standard procedures known to those skilled in the art. The drug may be prepared by standard procedures known to those skilled in the art, for example, reflected in "Pharmaceutics: The Science of Dosage Forms, second edition, Aulton, M. E. (Publisher) Churchill Livingstone, Edinburgh (2002); "Encyclopedia of Pharmaceutical Technology", second edition, Swarbrick, J. and Boylan J. C. (Publisher), Marcel Dekker, Inc. New York (2002); "Modern Pharmaceutics", fourth edition, Banker G. S. and Rhodes C. T. (Publisher) Marcel Dekker, Inc. New York 2002 and "The Theory and Practice of Industrial Pharmacy", Lachman L., Lieberman H. and Kanig J. (Publisher), Lea & Febiger, Philadelphia (1986). The respective descriptions are incorporated herein by reference and form part of the description. The composition of the drug may vary depending on the route of administration. Illustrative non-limiting examples of said pharmaceutical dosage forms of the pharmaceutical composition of the disclosure include oral or buccal formulations (liquid, solution, suspension, emulsion, gel, paste, powder, oral lyophilisate, tablets, capsules, pills, emulsions); sublingual formulations; ophthalmic formulations; ear (otic) formulations; topical formulations; nasal formulations; rectal formulations; vaginal formulations; intrauterine formulations; inhalation or pulmonary formulations; parenteral formulations, for example, injectable formulation, for example, for intravenous injections or for subcutaneous injections.

Preparation Method

Another advantage of the present disclosure is the ease with which the nanoparticles are prepared, a method that does not require injection or homogenisation. In general, the method comprises (i) the step of adding an organic solution comprising an organic solvent and a sorbitan ester to an aqueous solution; (ii) the step of evaporating the solvent, that is, the organic solvent, and the water; and (iii) an optional incubation step. The positively charged substance can be incorporated into the organic solution or the aqueous solution. On the other hand, the miRNA (or miRNAs) is incorporated, either during step (i) as part of the aqueous solution, or in the incubation step (iii), or in both steps (i) and (iii). In the case that no miRNa is incorporated during step (i), it is necessary to proceed with the incubation (step (iii)) to incorporate the miRNA (or the miRNAs). Thus, an alternative is a method comprising (i) the step of adding a solution comprising an organic solvent, a sorbitan ester, and a positively charged substance to an aqueous solution comprising a miRNA; and (ii) the step of evaporating the solvent, that is, the organic solvent, and the water. Another alternative comprises (i) the step of adding a solution comprising an organic solvent, a sorbitan ester, and a positively charged substance to an aqueous solution; (ii) the step of evaporating the solvent, that is, the organic solvent, and the water; and (iii) the step of incubating the nanoparticle resulting from step (ii) in the presence of a miRNA. Suitable procedures are described, for example, in WO2013/068625.

Below is a detailed description that will be complemented with the examples.

The addition of the organic phase is preferably carried out with stirring of the aqueous phase. The components that the system may additionally comprise, such as for example a negatively charged substance, may be added to the organic phase or the aqueous phase, depending on the characteristics of the substance being incorporated into the system. Thus, in a particular embodiment, the aqueous solution further comprises a negatively charged substance.

Alternatively, the additional components can be incorporated in a subsequent step, for example, step (iii) of incubation of the dispersion of nanoparticles formed with a solution comprising any of these substances.

Alternatively, it is possible to obtain pegylated or modified nanoparticles with ethylene oxide derivatives. These pegylated or modified nanoparticles with ethylene oxide derivatives can be prepared in a single step and furthermore have the advantage that no chemical reaction is necessary in order to anchor the ethylene oxide chains to the surface of the nanoparticles. Thus, in another particular embodiment, the organic phase further comprises an ethylene oxide derivative, for example, one of formula $R^{16}O[CH_2—CH_2—O]_f—C(H)(R^{17})(R^{18})$ as described above.

For the preparation of the nanoparticles of the disclosure, it is usually preferable that the solvent of the organic phase is a water-soluble solvent, for example, an aliphatic alcohol, such as ethanol, which is easy to evaporate, more harmless and stable against the components of the nanoparticles.

The concentrations of the different components is not critical. For example, the sorbitan ester is dissolved in the organic phase in a concentration, which may be between 0.1 and 10 mg/mL, or between 2 and 7 mg/mL. On the other hand, the positively charged substance may be in a concentration of between 0.01 and 5.0 mg/mL, for example, between 0.1 and 2.0 mg/mL preferably between 0.2 and 0.5 mg/mL. The negatively charged substance may be in a concentration of between 0.01 and 5.0 mg/mL, for example, between 0.05 and 2.0 mg/mL preferably between 0.1 and 0.3 mg/mL.

The mixture of the aqueous and organic phases can be performed at room temperature or by heating one or both phases.

It has been found that the nanoparticles of the disclosure withstand freeze-drying and other dehydration processes without degradation. Therefore, the method may comprise an additional step of total or partial dehydration (lyophilisation or desiccation, respectively). In this way, it is possible to preserve them during storage so that they retain their initial characteristics and reduce the volumes of product to be handled. The lyophilisation or drying process leads, respectively, to a totally or partially dehydrated product. In the case of dehydration, the method comprises an additional step in which partially dehydrated or lyophilised nanoparticles are regenerated. In this way, it is possible to dehydrate the nanoparticles to obtain a more stable product during storage and subsequently to regenerate or recover the nanoparticles by a process of re-suspension in an aqueous medium.

Thus, a final aspect of the disclosure is directed to nanoparticles obtainable as described above.

The components described above can be combined so that, in each case, the resulting nanoparticle of the disclosure is adapted to the particular situation, and the present disclosure encompasses various combinations of sorbitan esters, positively charged substances, miRNAs, as well as negatively charged substances and other optional components if used. For example, one embodiment of the present disclosure is a nanoparticle comprising (i) one or more miRNAs (e.g., miR-20a, miR-29, miR-652, or mixtures thereof); (ii) a sorbitan ester of formula I, as defined above; (iii) a positively charged substance of formula $(R)_{10})_p(R^{11})(R^{12})NR^9$, as described above; and (iv) a negatively charged polysaccharide. In another embodiment, the present disclosure comprises (i) one or more miRNAs (for example, miR-20a, miR-29, miR-652, or mixtures thereof, or also miR-93, or mixtures thereof with one or more of the previous ones); (ii) a sorbitan ester of formula I, as defined above; (iii) a positively charged substance selected from the group consisting of CTAB, BZC, oleylamine and mixtures thereof; and (iv) a negatively charged polysaccharide. Another embodiment of the present disclosure is a nanoparticle comprising (i) one or more miRNAs; (ii) a sorbitan ester of formula I, as defined above; (iii) a positively charged substance of formula $(R)^{10})_p(R^{11})(R^{12})NR^9$, as described above; and (iv) a negatively charged polysaccharide wherein at least one of its monomers comprises a —COOH or —SO3H group.

Another embodiment of the present disclosure is a nanoparticle comprising (i) one or more miRNAs; (ii) a sorbitan ester; (iii) a positively charged substance; and (iv) a positively charged polysaccharide wherein at least one of its monomers comprises a —COOH or —SO3H group. Another embodiment of the present disclosure is a nanoparticle comprising (i) one or more miRNAs; (ii) a sorbitan ester of formula I, as defined above; (iii) a positively charged substance of formula $(R)^{10})_p(R^{11})(R^{12})NR^9$, as described above; and (iv) a negatively charged polysaccharide. The above combinations and others that are not explicitly described are also part of the scope of protection.

It must be taken into account that, in addition to the miRNA, the nanoparticles of the disclosure may comprise other components, such as, for example, other active ingredients of interest, for which it would suffice to add them to the organic solution or the aqueous solution or both during the preparation of the nanoparticle. It would also be possible to add them during the additional step (iii) of incubation.

EXAMPLES

For the description of some of the following examples reference is made to results obtained by the following techniques:

The size of the nanoparticles was determined using the photon correlation spectroscopy (PCS) technique and using a Zeta Sizer (Zeta Sizer, Nano Series, Nano-ZS, Malvern Instruments, U.K.), obtaining the average population size and the polydispersion index thereof. The procedure comprises diluting the samples in Milli-Q water at a ratio of 1:19. Each analysis was carried out at 25° C. with a detection angle of 173°.

The zeta potential of the nanoparticles was detected by the laser dispersion anemometry (LDA) technique using a Zeta Sizer (Zeta Sizer, Nano series, Nano-ZS, Malvern Instruments, U.K.). The procedure comprises diluting the samples in millimolar KCl solution.

The efficiency of the association of the miRNAs with the nanoparticles was determined by the technique of agarose gel electrophoresis. The procedure comprises preparing 2% agarose gel in TAE buffer (Tris-Acetate-EDTA, 40 mM Tris, 1% acetic acid, 1 mM EDTA), pH 8 with SYBR®. Gold and glycerol nucleic acid gel stain was used as the charging substance. A potential difference of 25 mV was applied for 30 minutes and free miRNA was used as control.

As used in the following examples, the following polymers were purchased from different commercial establishments: hyaluronic acid (Bioibérica, Spain), chondroitin sulphate (Calbiochem, U.S.A.). Span® 80 and oleylamine were purchased from Sigma (Spain). The different miRNAs used were purchased from Exiqon (Denmark). The other products indicated in the examples below were purchased from Sigma (Spain).

To confirm the validity of the nanoparticles of the disclosure in a proof of concept, the assays described below were carried out in vitro and in vivo. These assays sought to, among other things, confirm the correct association of the miRNAs in the nanoparticles, their correct distribution to the relevant target cells, and their improved therapeutic effect.

Example 1: In Vivo Proof of Concept Study on the Therapeutic Effect in Terms of Clinical Regulation of the Provided Liver Metastases Preparation and Characterisation of Nanoparticles For the preparation of the nanoparticles, a solution of sorbitan monooleate (Span® 80, SP80) and oleylamine (OA) in 3 mL of ethanol (organic phase) was prepared at a concentration of 6.6 and 0.33 mg/mL respectively. Then, this organic phase was added to 6 mL of a stirred aqueous phase containing chondroitin sulphate (CS) at a concentration of 0.125 mg/mL, thereby resulting in the spontaneous formation of NPs. The ethanol was finally removed under reduced pressure in a rotary evaporator. The miRNA was included in the aqueous phase at a concentration of 8.33 µg/mL during the preparation of the nanoparticles. For this purpose, miR-20a was selected. These proportions correspond to percentages by weight based on the total weight of the nanoparticle of 91.67% SP80, 4.63% OA, 3.47% CS, and 0.23% miR-20a.

The size and zeta potential of the nanoparticles were measured by photon correlation spectroscopy and laser Doppler anemometry, respectively.

TABLE 1

Physical-chemical characteristics of the nanoparticles of the disclosure

| Formulation | size (nm) | PdI | ζ Potential |
|---|---|---|---|
| SP80-OA-CS | 115.9 ± 15.6 | 0.073 | −37.5 ± 1.5 |
| SP80-OA-CS-miR20 (50 µg/mL miR-20a) | 144.1 ± 1.7 | 0.062 | −31.9 ± 2.1 |

Efficiency of the Association Between the miRNA and the Nanoparticle

The loading efficiency of the microRNA to the nanoparticles was confirmed by the agarose gel electrophoresis technique, as illustrated in FIG. 1.

Animal Handling:

All the experiments described in this work have been carried out in accordance with Spanish and European laws concerning the care of animals for experimentation. The animal handling and the experimental methods of our laboratory have been analysed and approved by the Animal Experimentation Committee of the University of the Basque Country, Spain. Every effort was made to minimise the number of animals used and their suffering. C57 BL/6NCrl mice (females, 8 weeks old) were obtained from Charles River Laboratories España, S.A. The mice were housed in the Biological Resources Unit of the University of the Basque Country and kept in a controlled temperature environment (21±1° C.), with relative humidity of 55±5%, a light/dark cycle of 08:00 a.m.-08:00 p.m., and conventional mouse food and water were given ad libitum.

Liver Metastasis Model and Clinical Evaluation:

A liver metastasis model was developed by injecting into the mice a c26 murine colorectal cancer cell line (200,000 cells/animal). The animals were anesthetised with isoflurane (5% and 1.5% for maintenance) and the cells were injected into the spleen. After the intervention, the incisions were sutured. The animals were treated on day 3 after the tumour inoculation and subsequently every 3 days until day 21 with a total dose of 25 µg of miRNA per animal. The mice were separated into 5 different groups depending on the treatment. Group 1 was treated with placebo (glucose); group 2, according to the disclosure, was treated with SP80-OA-CS nanoparticles associated with miR-20α with a fluorescent marker (6-carboxyfluorescein) (FAM); group 3 was treated with free or naked miR-20a (without any specific vehicle); group 4 was treated with SP80-OA-CS nanoparticles associated with a miRControl (this miR does not attack any mRNA); group 5 was treated with blank SP80-OA-CS nanoparticles (without associated mRNA). On day 21 after inoculation, the animals were sacrificed and the livers were observed and then processed for histological analysis.

Histology:

After cervical dislocation, the livers were rapidly removed and fixed in paraformaldehyde (4% PFA) in PBS, overnight at 4° C. The fixed livers were processed for inclusion in paraffin. Serial sections of 10 µm thickness were mounted in five parallel series and processed for haematoxylin-eosin staining. Microscopic images were captured in a Zeiss microscope.

Some liver sections were observed 48 hours after the last injection. The sections were incubated with anti-mannose receptor marker and Alexa 593 anti-mouse antibody. The green marker of miR-20a (FAM) was observed within the endothelial cells marked in red, confirming the endothelial attack or the specific distribution to the liver sinusoidal endothelial cells (LSEC) provided by the nanoparticles to the miR-20a.

After the macroscopic evaluation of the livers the therapeutic effect in terms of clinical regulation of the liver metastases in the group of animals treated with SP80-OA-CS associated with miRNA-20a (FIG. 2) was confirmed.

Figure 2:
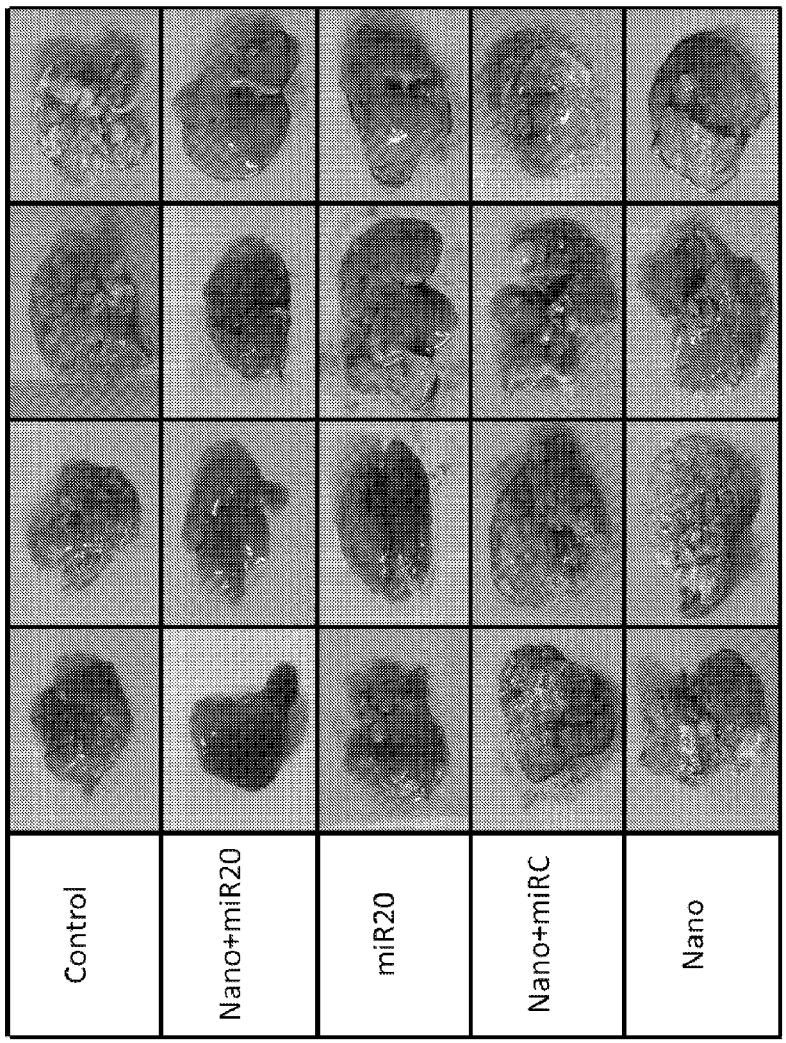
FIG. 2. Demonstration of the therapeutic effect in vivo. Clinical regulation of liver metastasis using nanoparticles SP80-OA-CS-miR-20a according to the disclosure. Murine colorectal cancer C26 cell lines (200,000 cells/animal) were injected into mice. The animals were treated from day 3 after tumour inoculation, and subsequently every 3 days until day 21. On day 21, the animals were sacrificed and their livers were processed for histological analysis. The mice were separated into 5 treatment groups. Group 1 was treated with placebo (glucose); group 2 (according to the disclosure) with SP80-OA-CS-miRNA-20a; group 3 with free miRNA-20a, without any specific vehicle; group 4 with a nanoparticle SP80-OA-CS associated with a miRControl (a miRNA that does not attack any target); group 5 with nanoparticles SP80-OA-CS without any miRNA. The macroscopic evaluation of the livers confirmed the therapeutic effect in terms of clinical regulation in the animals treated with SP80-OA-CS-miRNA-20a (group 2).
Figure 3:
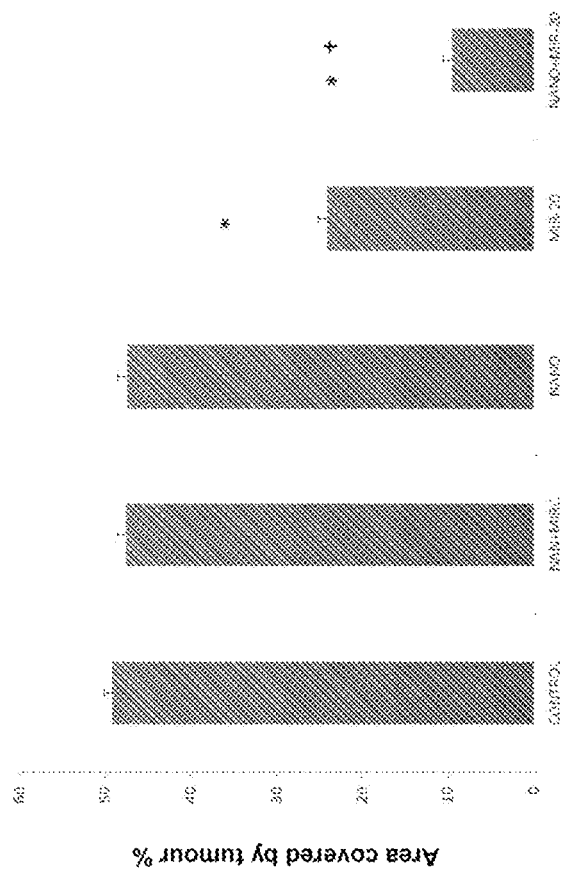
FIG. 3. Demonstration of the therapeutic effect in vivo. Histological analysis. Sections of the livers evaluated in FIG. 2 were stained with haematoxylin-eosin, and the area covered by the tumour was quantified under the microscope. The different groups were related to the control group (group 1 treated with placebo) by means of the T-test. Significant statistical differences ($p<0.05$) are marked with an *. Group 2 (treated with SP80-OA-CS-miRNA-20a) was also compared with group 5 (treated with SP80-OA-CS without miRNA) and its significant statistical difference ($p<0.05$) is indicated with a +.

The sections of the livers in FIG. 2 were stained with haematoxylin-eosin and the area covered by the tumour was quantified under the microscope. The different groups were related to the control group (treated with glucose as a placebo) by means of the T-test. Significant statistical differences ($p<0.05$) are indicated with an *. Likewise, the group treated with SP80-OA-CS nanoparticles associated with miR-20a and with blank SP80-OA-CS nanoparticles (without associated mRNA) were compared and the statistically significant difference ($p<0.05$) was indicated with a +. As can be seen in FIG. 3, the area covered by the tumour was surprisingly smaller in mice treated with SP80-OA-CS nanoparticles associated with miR-20a (according to the disclosure) than in mice treated only with miR-20a.

This confirms an improvement impossible to anticipate a priori of the nanoparticles according to the disclosure in the in vivo vehiculisation of miRNAs. Moreover, the therapeutic effect provided by these nanoparticles in terms of clinical regulation of liver metastases is surprising.

Example 2: In Vivo and In Vitro Additional Proof of Concept Study on the Therapeutic Effect and the Behaviour of the Nanoparticles of the Disclosure Colorectal Cancer Cells Syngeneic cell lines of c26 murine colorectal cancer (ATCC, Manassas, Va., U.S.A.) were used with Balb/c mice. The cells were cultured under standard conditions in RPMI medium (Sigma-Aldrich, St. Louis, Mo., U.S.A.), supplemented with 10% fetal bovine serum (FBS), penicillin (100 U/mL), streptomycin (100 μg/mL) and amphotericin B (0.25 μg/mL), all purchased from Life Technologies, Carlsbad, Calif., U.S.A.)

Control and Tumour-Activated Cells

The mice were anesthetised with isoflurane, and a small incision was made in their left side. Then, the cut was inoculated with 50 μl of the C26 cancer cells at a concentration of $2\times10^6$ cells/mL. Next, the peritoneum and skin were sutured. The control mice were inoculated with PBS. Fourteen days later, all the mice were sacrificed and the cancer activated cell lines and control lines were isolated by Percoll differential gradient centrifugation (25% to 50%) (Sigma-Aldrich, St. Louis, Mo., U.S.A.). Cell lines were seeded with RPMI 1640 medium with 10% FBS, and RNA purification was performed following the protocol of a Purelink RNA minikit (Gibco Life Technologies Inc., Gaithersburg, Md., U.S.A.).

Figure 4:
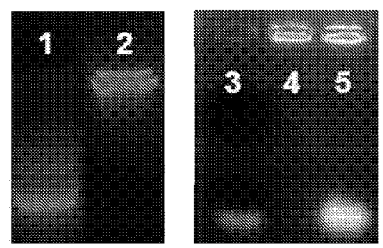
FIG. 4. Electrophoresis gel confirming the existence of an effective association between a miRNA or a plasmid (pEGFP) and the nanoparticles prepared in Example 2. 1) band corresponding to free pEGFP (200 µg/mL), 2) band corresponding to nanoparticles associated with pEGFP 200 µg/mL, 3) band corresponding to free miR-20a (5 µg/mL), 4) band corresponding to nanoparticles associated with miR-20a 50 µg/mL (according to the disclosure), 5) band of the mixture of nanoparticles and miR-20a 100 µg/mL (non associated).

Preparation and Characterisation of Control SP-OA-CS, SP-OA-CS Associated with pEGFP, and SP-OA-CS Associated with miRNA Following an analogous scheme to that of Example 1, the nanoparticles described below were prepared. A solution of sorbitan monooleate (Span 80, SP) and oleylamine (OA) (Sigma-Aldrich, St. Louis, Mo., U.S.A.) was prepared in ethanol at a concentration of 6.6 and 0.33 mg/mL, respectively. Then, this organic phase was added with magnetic stirring to an aqueous phase containing chondroitin sulphate (CS) (Calbiochem, U.S.A.) at a concentration of 0.125 mg/mL, in a volume ratio of 1:2, respectively. The ethanol was removed under reduced pressure in a rotary evaporator. For the encapsulation of genetic material, this was included in the aqueous phase during the construction of the nanoparticles at concentrations of 33.3 μg/mL for Enhanced Green Fluorescent Protein plasmid (pEGFP) (Elim Biopharmaceutics, U.S.A.) and 8.33 μg/mL and 16.7 μg/mL for miRNA (miR-20 or miR-control) (Exiqon, Denmark). The final formulations obtained were 200 μg/mL of NP loaded with pEGFP, 50 and 100 μg/mL of NP loaded with miRNA. The formulations were administered in a 5% glucose solution for the in vivo studies. The efficiency of the association of the plasmid DNA and the miRNAs was determined by agarose gel electrophoresis, with results analogous to those of Example 1, confirming that the migration of the nucleic acids to the gel was prevented by their association with the nanoparticles; no free genetic material was observed in these formulations (see FIG. 4). The morphology of the nanoparticles was examined with transmission electron microscopy (CM 12 Philips, Eindhoven, The Netherlands) after staining with 2% w/v phosphotungstic acid solution. For this purpose, the samples were placed in copper grids (400 mesh) covered with a Formvar® film.

Figure 5:
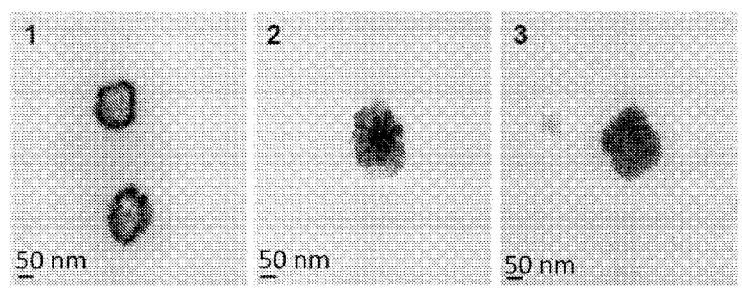

The blank nanoparticles (without genetic material incorporated) and the nanoparticles associated with pEGFP or miR-20a had nanometric sizes of 133 nm, 143 nm, and 143 nm, and negative surface charges of −38 mV, −36 mV and −33 mV, respectively. The morphology of the nanosystems was observed using transmission electron microscopy (TEM). The TEM images confirmed the nanometre size of the formulations (FIG. 5).

TABLE 2

Physicochemical characterisation of SP-OA-CS nanoparticles associated with pEGFP or with miR-20a that are able to target LSEC in vitro and in vivo

| Formulation | Size (nm) | PdI | Potential ζ (mV) |
|---|---|---|---|
| SP-OA-CS | 132.9 ± 4.2 | 0.069 | −38.2 ± 1.6 |
| SP-OA-CS-pEGFP | 142.7 ± 13.8 | 0.091 | −36.4 ± 8.6 |
| SP-OA-CS-miR-20a | 142.6 ± 1.4 | 0.065 | −33.3 ± 3.0 |

Correct Distribution of the Nanoparticles of the Disclosure to the Relevant Target Cells To demonstrate the cellular uptake and transfection ability of SP-OA-CS nanoparticles by LSEC, a plasmid DNA encoding GFP was incorporated during their preparation. The expression of GFP was evaluated 24 h after transfection using fluorescence microscopy. At this experimental time, the LSECs expressed GFP, which indicates the internalisation of nanoparticles and the supply of successful plasmids, that is, the efficient release of genetic material to said cells by the nanoparticles. To evaluate if the nanoparticles of the disclosure could be effective in LSEC in vivo, they were injected systemically into SP-OA-CS mice containing EGFP plasmid. The liver sinusoids expressed GFP, indicating successful plasmid delivery, that is, the efficient release of genetic material to said cells by the nanoparticles. In addition, the sections were immunostained with anti-mannose receptor and F4/80 antibodies. The GFP-positive cells were liver sinusoidal endothelial cells. The fluorescence signal of miR-20a was detected in LSEC when mice were injected with nanoparticles associated with miRNA. At the same time, the fluorescent signal was wider when miR-20a was injected in the naked form.

Figure 6:
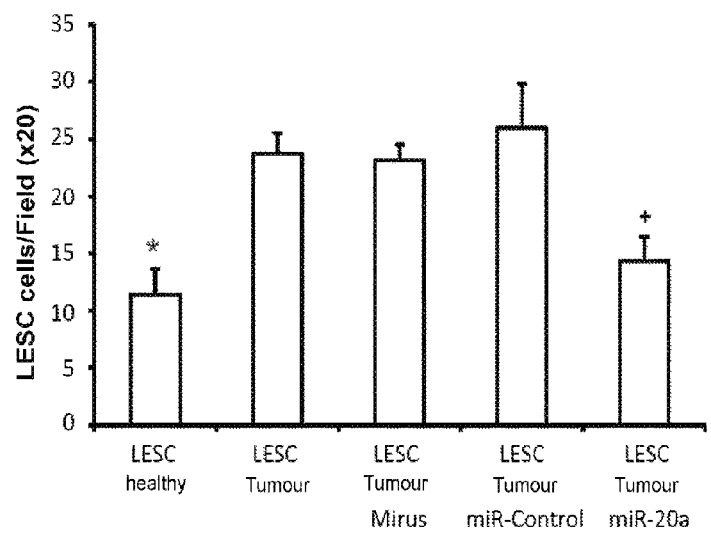
FIG. 6: LSEC migration ability (Example 3). The * reflects the statistical significance, the difference between healthy LSEC compared to liver LSEC colonised by the tumour; and + indicates the statistical significance of the difference between liver LSEC colonised by the tumour and liver LSEC colonised by the tumour but transfected with miR-20a. In both cases a threshold of $p<0.05$ was used.

Example 3: Increased Migratory Capacity of LSECs Activated by Tumour Signals is Prevented by miR-20a To verify whether miR-20a ablation in LSEC from tumour-colonised livers had any consequence on the physiological behaviour of these cells, they were cultivated in collagen-coated 8-μm pore inserts to measure their migration ability. The tumour-activated LSECs were treated with miR-20a, with miR control or with the unloaded transfection vehicle Myrus®. It was found that the LSEC migration ability increased approximately two-fold when the cells were activated by the tumour, but this was almost reversed to basal levels when the cells were transfected with exogenous miR-20a (p<0.05). Therefore, restoring cellular miR-20a expression in LSECs was sufficient to prevent the increased migratory ability associated with tumour-induced activation (FIG. 6).

Figure 7:
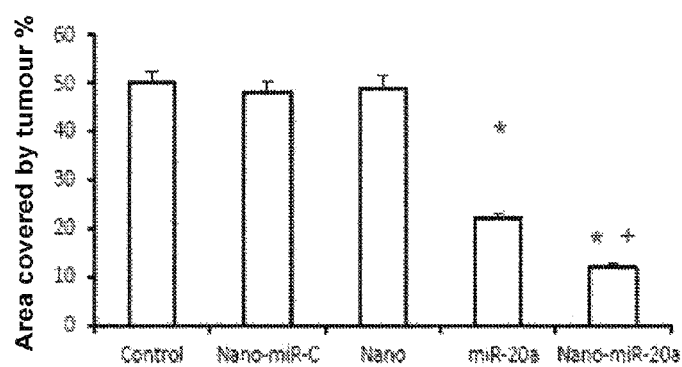
FIG. 7. Demonstration of the therapeutic effect in vivo for the second proof of concept (Example 4). Histological analysis. Sections of the livers evaluated were stained with haematoxylin-eosin, and the area covered by the tumour was quantified under the microscope. The different groups were related to the control group (group 1 treated with placebo) by means of the T-test. Significant statistical differences ($p<0.05$) are marked with an *. Group 2 (treated with SP80-OA-CS-miRNA-20a) was also compared with group 5 (treated with SP80-OA-CS without miRNA) and its significant statistical difference ($p<0.05$) is indicated with a +.

Example 4: In Vivo Colorectal Cancer Liver Metastasis Development and Histological Liver Tissue Analysis Following a methodology analogous to that of Example 1, Balb/c mice were anesthetised with isoflurane (Esteve, Spain), and a small cut was made on their left side. Then, the spleen was exposed to perform an intra-splenic inoculation of 50 μl of C26 colon carcinoma cells at a concentration of $2 \times 10^6$ cells/mL for each mouse. The animals were divided into 5 groups, and the treatments were performed every 3 days from the day of the inoculation of cancer cells. Group 1 was treated with placebo (glucose); group 2, according to the disclosure, was treated with SP80-OA-CS nanoparticles associated with miR-20a; group 3 was treated with free or naked miR-20a (without any specific vehicle); group 4 was treated with SP80-OA-CS nanoparticles associated with a miRControl (this miR does not attack any mRNA); group 5 was treated with blank SP80-OA-CS nanoparticles (without associated mRNA). Finally, the livers were embedded in paraffin and frozen for histological analysis. To quantify the area covered by the tumour, consecutive 7 μm sections were cut with 500 μm between them in paraffin-embedded livers. Next, staining with haematoxylin and eosin was performed, and the tumour area was quantified using ImageJ Software. In addition, to analyse the potentially activated infiltrating LSECs in the metastasised area, immunostaining with 1:100 dilution of anti-CD31 monoclonal antibody was performed (BD Pharmingen, U.S.A.), followed by the appropriate secondary fluorescent Alexa 594 antibody (1:1000). The images were quantified using the AnalySIS V3.2 program (Olympus Software Imagine Solutions GmbH, Munster, Germany). The results are expressed as a percentage of specifically coloured tissue area relative to the entire analysed area. The results are shown in FIG. 7.

Example 5: E2F1 and ARHGAP1 miR-20a Target Proteins were Downregulated in Tumour-Colonised LSECs Relative to Healthy LSECs The miRBASE database (www.mirbase.org) was used to identify 713 proteins as possible miR-20a targets. In parallel, in a proteomic study, 174 proteins were identified that were upregulated in tumour-activated LSECs compared to control LSECs. When both sets of data were compared, 5 coincidentally expressed proteins were found: E2F1, JAK1, ARHGAP1, ACSL4, and DECR1.

A Western blot analysis was then performed with tumour-activated LSECs and tumour-activated LSEC cultured with exogenous miR20a. Briefly, LSEC cultures were lysed with RIPA buffer, separated through 8% SDS-PAGE electrophoresis and transferred to a nitrocellulose membrane (Bio-Rad Laboratories, Hercules, Calif., U.S.A.). E2F1 (Santa Cruz Biotechnology, Dallas, Tex., U.S.A.) and ARHGAP1 (Abcam, Cambridge, U.K.) (1:1000) were detected using protein A conjugated with horseradish peroxidase (1:5,000) (Sigma-Aldrich St. Louis, Mo., U.S.A.). The bands were visualised using a Femto Super Signal Substrate kit (Pierce Chemical Co, Rockford, Ill., U.S.A.). GAPDH was used as a protein loading control.

Figure 8:
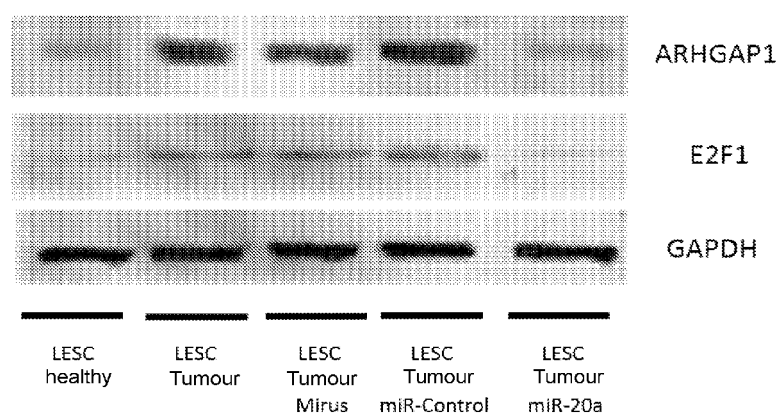

Under control conditions, E2F1 and ARHGAP1 showed low expression. However, after the activation of LSEC with the tumour, both E2F1 and ARHGAP1 were largely upregulated. When cells were transfected in vitro with miR-20a, the protein expression was reduced in both cases to basal levels (see FIG. 8).

Example 6: Lyophilisation

The nanoparticles developed in Example 1 were evaluated with respect to their ability to maintain the association with the miRNA after a lyophilisation process.

The invention claimed is:

1. A nanoparticle comprising (i) between 60% and 99% by weight, based on the total weight of the nanoparticle, of a sorbitan ester; (ii) a positively charged substance, (iii) miR-20a, and (iv) a negatively charged substance.

2. The nanoparticle according to claim 1, wherein said positively charged substance has the formula $(R^{10})_p(R^{11})(R^{12})NR^9$, where
   each of $R^{10}$, $R^{11}$, and $R^{12}$ is independently selected from the group consisting of
   —H, $C_1$-$C_4$ alkyl, $C_2$-$C_4$ alkenyl, $C_2$-$C_4$ alkynyl, and $C_7$-$C_{15}$ phenylalkyl;
   $R^9$ is selected from the group consisting of $C_1$-$C_{40}$ alkyl, $C_2$-$C_{40}$ alkenyl, and $C_2$-$C_{40}$ alkynyl;
   p is 0 or 1
   and wherein it also comprises a counter-anion when p is 1.

3. The nanoparticle according to claim 1, wherein said positively charged substance is selected from the group consisting of oleylamine, benzalkonium chloride and cetyl trimethyl ammonium bromide.

4. The nanoparticle according to claim 1, wherein said sorbitan ester comprises a compound of formula I

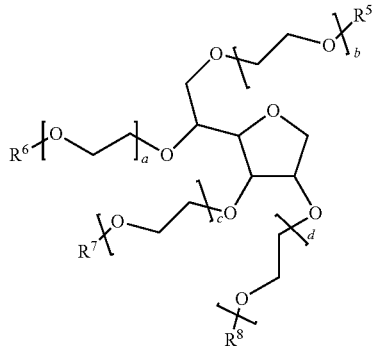

Formula I where each of $R^5$, $R^6$, $R^7$, and $R^8$ is independently selected from the group consisting of —H, —(C=O)—$C_1$-$C_{40}$ alkyl, —(C=O)—$C_2$-$C_{40}$ alkenyl, and —(C=O)—$C_2$-$C_{40}$ alkynyl, with the proviso that at least one of $R^5$, $R^6$, $R^7$ and $R^8$ is not —H;

and each of a, b, c and d is independently a number between 0 and 100.

5. The nanoparticle according to claim 4, wherein said alkyl group is linear and comprises between 2 and 20 carbon atoms.

6. The nanoparticle according to claim 4, wherein said sorbitan ester has the formula II

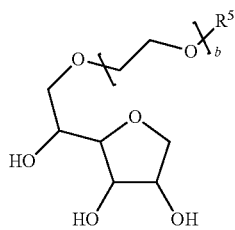

Formula II where
$R^5$ is selected from the group consisting of —(C=O)—$C_1$-$C_{40}$ alkyl and —(C=O)—$C_2$-$C_{40}$ alkenyl; and
b is a number between 0 and 100.

7. The nanoparticle according to claim 6, wherein b is 0; and $R^5$ has the formula —$(CH_2)_n$—CH=CH—$(CH_2)_m$—$CH_3$, where n is an integer between 1 and 10, and m is an integer between 1 and 10.

8. The nanoparticle according to claim 1, wherein said negatively charged substance comprises a polysaccharide whose repeating unit has the formula $[X\text{-}Y\text{-}(Z)_n]$ where n is 0 or 1; X, Y, and Z are each independently selected from the group consisting of monosaccharides, disaccharides, and polysaccharides; with the proviso that at least one of X, Y, and Z comprises an acid sugar and wherein the X, Y, and Z groups are linked together through —O-glycosidic bonds.

9. The nanoparticle according to claim 8, wherein Y comprises an acid sugar.

10. The nanoparticle according to claim 9, wherein Y comprises an uronic acid.

11. The nanoparticle according claim 10, wherein said uronic acid has the formula III

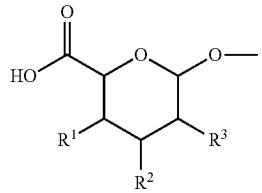

Formula III where
each of $R^2$, and $R^3$ is independently selected from the group consisting of —H, —OH, —O—, —$OR^4$, N(H)—$R^4$ and —O—$SO_3$, with the proviso that at least one of $R^2$, and $R^3$ is —O—,
where —O— is the oxygen atom that forms the glycosidic bond, and
where $R^4$ is selected from the group consisting of $C_1$-$C_4$ alkyl, $C_2$-$C_4$ alkenyl, $C_2$-$C_4$ alkynyl, —(C=O)—$C_1$-$C_4$ alkyl, —(C=O)—$C_2$-$C_4$ alkenyl, and —(C=O)—$C_2$-$C_4$ alkynyl.

12. The nanoparticle according to claim 1, wherein said negatively charged substance is a polysaccharide comprising one or more carboxylic groups.

13. The nanoparticle according to claim 12, wherein said negatively charged substance comprises glucuronic acid in its repeating structure.

14. The nanoparticle according to claim 1, wherein said negatively charged substance is selected from the group consisting of hyaluronic acid, chondroitin sulphate, and xanthan gum.

15. The nanoparticle according to claim 1, wherein it has a negative potential comprised between −25 and −40 mV.

16. A pharmaceutical composition comprising the nanoparticle as defined in claim 1, and a pharmaceutically acceptable excipient.

17. A method of inhibiting liver metastasis progression comprising administering the nanoparticle of claim 1 to a subject in need of inhibition of liver metastasis progression.

* * * * *